United States Patent
Fu et al.

(10) Patent No.: US 7,091,205 B2
(45) Date of Patent: Aug. 15, 2006

(54) USE OF TETRAMETHYLPYRAZINE IN THE TREATMENT OF BRAIN TUMOR

(76) Inventors: Yu Show Fu, No. 155, Sec. 2, Li-Nung St., Pei-Tou Dist., Taipei (TW); Henrich Cheng, No. 322 Shih-Pai Road, Sec. 2, Pei-Tou Dist., Taipei (TW)

( * ) Notice: Subject to any disclaimer, the term of this patent is extended or adjusted under 35 U.S.C. 154(b) by 0 days.

(21) Appl. No.: 10/961,840

(22) Filed: Oct. 8, 2004

(65) Prior Publication Data

US 2006/0079532 A1    Apr. 13, 2006

(51) Int. Cl.
*A61K 31/4965* (2006.01)
*A61P 35/00* (2006.01)

(52) U.S. Cl. .................... 514/252.1; 514/247

(58) Field of Classification Search .............. 514/247, 514/252.1
See application file for complete search history.

(56) References Cited

OTHER PUBLICATIONS

HCAPLUS DN: 138:276225, Zhao et al., CN 1362064 A Aug. 7, 2002, abstract only.*

HCAPLUS DN:119:85568, Liu et al., Zhongguo Yaolixue Yu Dulixue Zazhi, 7(2), 149-52 (1993), abstract only.*

Takano, T., et al., "Glutamate release promotes growth of malignant gliomas," *Nature Medicine*, 7(9):1010-1015 (2001).

Ishiuchi, I., et al., "Blockage of $Ca^{2+}$-permeable AMPA receptors suppresses migration and induces apoptosis in human glioblastoma cells," *Nature Medicine*, 8(9):971-978 (2002).

Tsai, T., et. al., "Pharmacokinetics of tetramethylpyrazine in rat blood and brain using microdialysis," *International Journal of Pharmaceutics*, 216:61-66 (2001).

Shih, Y., et al., "Protective effects of tetramethylopyrazine on kainite-induced excitotoxicity in hippocampal culture," *NeuroReport*, 13(4):515-519 (2002).

Pang, P., et al., "Tetramethylpyrazine, a Calcium Antagonist," *Planta Medica*, 62:431-435 (1996).

Ye, Z-C, et al., "Glioma Cells Release Excitotoxic Concentrations of Glutamate," *Cancer Research*, 59:4383-4391 (Sep. 1, 1999).

* cited by examiner

*Primary Examiner*—Christopher S. F. Low
*Assistant Examiner*—C. Delacroix-Muirheid
(74) *Attorney, Agent, or Firm*—Akin Gump Strauss Hauer & Feld, LLP

(57) ABSTRACT

The present invention relates to the use of tetramethylpyrazine (TMP) in the treatment of brain tumor.

11 Claims, 6 Drawing Sheets

USE OF TETRAMETHYLPYRAZINE IN THE TREATMENT OF BRAIN TUMOR

FIELD OF THE INVENTION

The present invention relates to the use of tetramethylpyrazine (TMP) in the treatment of brain tumor.

BACKGROUND OF THE INVENTION

According to the publications of the World Health Organism (WHO), there are nine types of brain tumors. Glioma is the most frequently found brain tumor, and cannot be easily diagnosed at its early stage, and it grows quickly. Although glioma can be removed through a surgical operation, the effect of the operation is generally unsatisfactory. Up to the present, glioma is still considered clinically as a problematic neurodisease. Glioma may result from mutation of normal glial cells in various brain regions. The growth of the tumor is accompanied with pathological symptoms such as elevated brain pressure, headache, vomiting, loss of sight and epilepsy. Most patients die within one year after the onset of glioma (Benedetti et al., 2000).

A previous study indicates that glioma cells release a large amount of glutamate, resulting in an elevated glutamate concentration in the periphery. The elevated glutamate concentration results in excitotoxicity to the surrounding neurons, and the damage to the neurons in turn promotes the growth of the glioma cells (Takano et al., 2001). Therefore, the reduction of the damage resulting from the excitotoxicity to neurons should be able to inhibit the growth of glioma cells.

Another study indicates that the elevated $Ca^{2+}$ concentration within glioma cells increases cell activity and thus contributes to the migration of glioma cells. Therefore a $Ca^{2+}$ channel blocker, such as MK801, can effectively inhibit the proliferation of glioma cells (Ishiuchi et al., 2002). However, MK801 is an antagonist of NMDA receptors, and will result in serious side effects when administered to patients.

Chuanxiong, a Chinese herbal medicine, is generally used in the treatment of brain vascular or cardiovascular embolism. Tetramethylpyrazine (TMP) is one of the major components in chuanxiong. Most of the TMP-related research focuses on the cardiovascular system. Relevant studies indicate that TMP can inhibit the increase of the concentration of calcium (Pang et al., 1996). As to the effect of TMP on neurons, we find TMP can reduce the excitotoxicity to neurons induced by kainite through protecting mitochondria and inhibiting the free radical generation (Shih et al, 2002).

It has also been reported that TMP can cross the blood-brain barrier (Tsai and Liang, 2001).

SUMMARY OF THE INVENTION

The present invention relates to the use of tetramethylpyrazine (TMP) in the treatment of brain tumor.

In one aspect, the present invention provides a method for treating brain tumor in a subject in need thereof, comprising administering a therapeutically effective amount of TMP to said subject.

In another aspect, the present invention provides a pharmaceutical composition for treating brain tumor, comprising a therapeutically effective amount of TMP and a pharmaceutically acceptable carrier.

In a preferred embodiment, the brain tumor to be treated is a glioma.

DETAILED DESCRIPTION OF THE INVENTION

Figure 1:
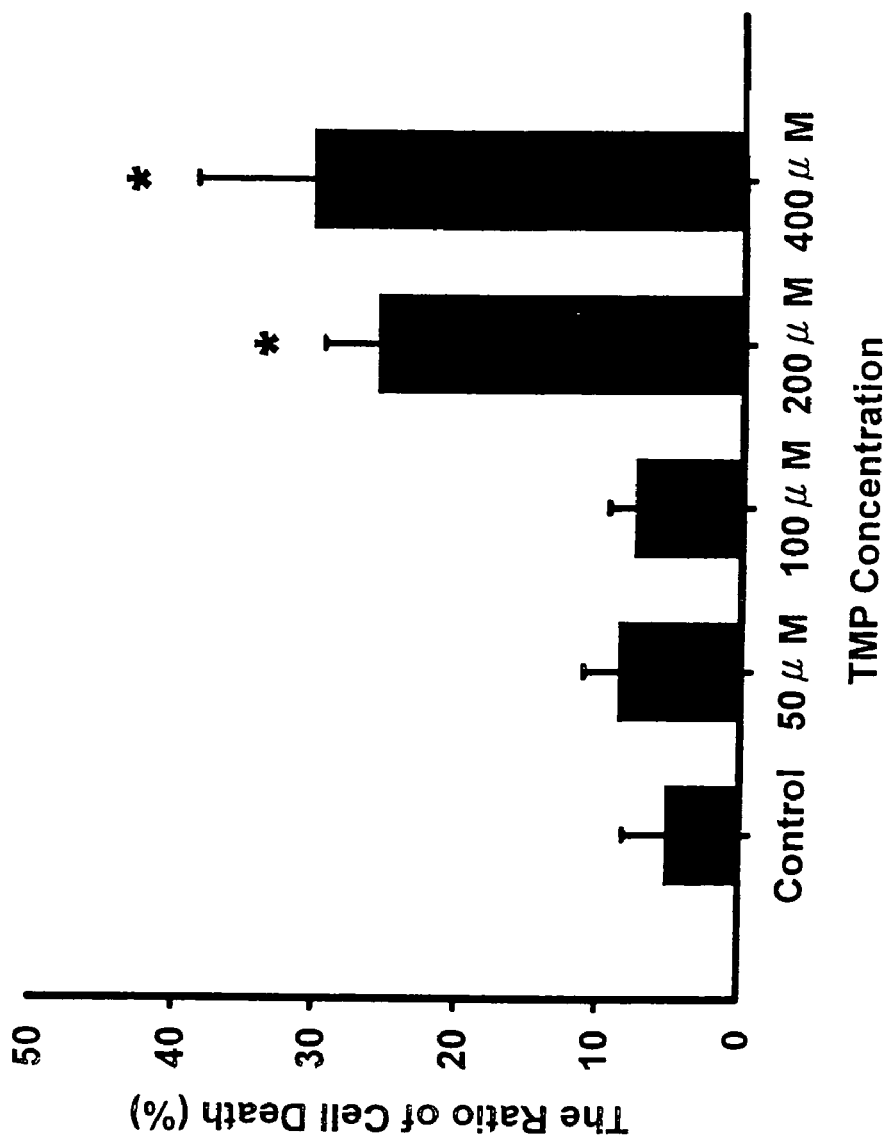
FIG. 1 shows the damage to glioma cells induced by TMP.

An embodiment of the present invention is a method for treating brain tumor in a subject in need thereof, comprising administering a therapeutically effective amount of TMP to said subject.

The term "subject" as used herein refers to an animal, preferably a mammal, most preferably a human.

The brain tumor to be treated may be any tumor that grows in the brain, including, but not limited to, glioma, glioblastoma, medulloblastoma, astrocytoma, and other primitive neuroectoderma.

TMP may be administered by any conventional route of administration including, but not limited to, oral, pulmonary, intraperitoneal (ip), intravenous (iv), intramuscular (im), subcutaneous (sc), transdermal, buccal, nasal, sublingual, ocular, rectal and vaginal. It will be readily apparent to those skilled in the art that any dosage or frequency of administration that provides the desired therapeutic effect is suitable for use in the present invention.

The therapeutically effect amount of TMP may be 5–4000 mg/Kg/day, preferably 10–1000 mg/Kg/day, more preferably 50–400 mg/Kg/day.

The dosages, however, may be varied depending on the requirements of the subject to be treated, including sex, age, weight, diet, etc. The precise amount of TMP required to be administered depends on the judgment of the practitioner and is peculiar to each individual.

Another embodiment of the present invention is a pharmaceutical composition for treating brain tumor, comprising a therapeutically effective amount of TMP and a pharmaceutically acceptable carrier.

To prepare a pharmaceutical composition of the present invention, TMP is admixed with a pharmaceutically acceptable carrier according to conventional pharmaceutical compounding techniques, wherein the carrier may take a wide variety of forms depending on the form of preparation desired for administration. Suitable pharmaceutically acceptable carriers are well known in the art. Descriptions of some pharmaceutically acceptable carriers may be found in The Hand Book of Pharmaceutical Excipients, published by the American Pharmaceutical Association and the Pharmaceutical Society of Great Britain.

The pharmaceutical composition of the present invention may be in the form of a tablet, pill, capsule, granule, powder, sterile parenteral solution or suspension, metered aerosol or liquid spray, or suppository, depending on the administration route.

As a solid dosage form, the pharmaceutical composition of the present invention may comprise, in addition to TMP, at least one diluent, binder, adhesive, disintegrant, lubricant, antiadherent, and/or glidant. Additionally, sweeteners, flavorants, colorants and/or coatings may be added for specific purposes.

As a liquid dosage form, the pharmaceutical composition of the present invention may comprise, in addition to TMP and a liquid vehicle, at least one wetting agent, dispersant, flocculation agent, thickener, buffer, osmotic agent, coloring agent, flavor, fragrance, and/or preservative.

The effect of TMP on glioma was evaluated in the following experimental examples, which are intended to be a way of illustrating but not limiting the present invention.

EXAMPLE 1

In Vitro Experiment 1-1 Culture of Rat C6 Glioma Cell Line

The rat C6 glioma cell line was purchased from the Food Industry Research and Development Institute, Taiwan. The cell culture within the tubes was transferred into a 15 ml centrifugation tube and centrifuged at 900 rpm for 3 minutes. Resulted supernatant was removed and 4 ml 10% FBS-DMEM was added to the centrifugation tube and sufficiently mixed with the cell pellet. The cells were counted and cultured in a 24-well plate ($2 \times 10^4$ cells per well) for subsequent in vitro experiments.

1-2 Treatment with TMP

The cultured C6 glioma cells were treated with TMP (Fluka, F-87915) at final concentrations of 50 μM, 100 μM, 200 μM, and 400 μM for 24 hours.

1-3 Determination of Cell Death

The degree of damage to glioma cells was measured as the intensity of propidium iodide (PI) fluorescence. PI is a fluorescent dye that binds DNA, with an excitation wavelength of 485 nm and an emission wavelength of 620 nm. When a cell is damaged, the permeability of the cell membrane is increased and PI can enter the cell to bind DNA.

The TMP-treated glioma cells were treated with 5 ng/ml PI (Molecular Probes, P-1304) for 1 hour, and then washed with 0.1 M PBS. The intensity of PI fluorescence was read by flow cytometry (FACSort). The results were shown in FIG. 1. As can be seen from FIG. 1, 200 μM and 400 μM TMP resulted in glioma cell death ($p<0.05$, *=significant difference from the control group).

1-4 Determination of $Ca^{2+}$ Permeability

Figure 2:
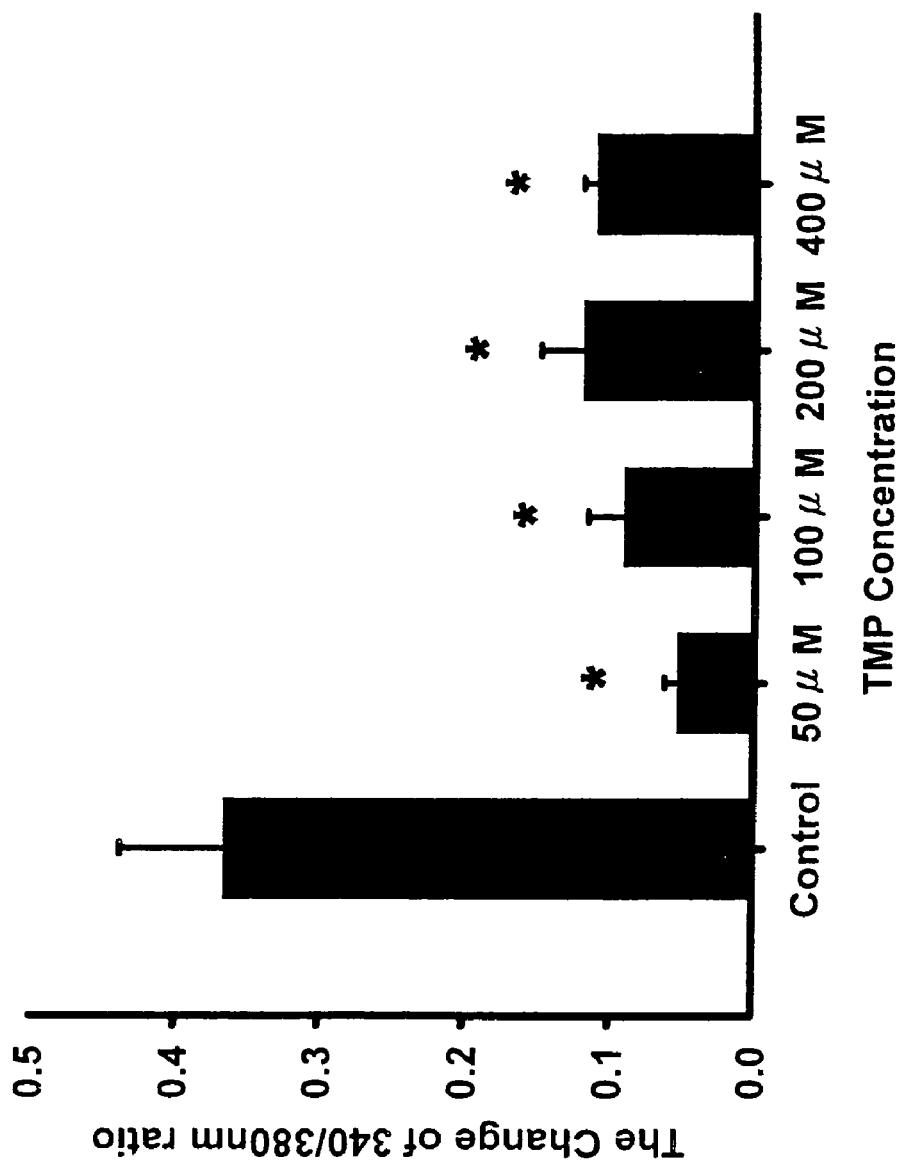
FIG. 2 shows TMP inhibit the increase of the concentration of $Ca^{2+}$ in glioma cells induced by glutamate.

The TMP-treated glioma cells were washed with running buffer for three times, put in a 5 μM Fura-2 AM solution for 30 minutes, and treated with 200 μM glutamate for 20 seconds. The change of $Ca^{2+}$ concentration within glioma cells was observed on a fluorescence microscope (IX-70, Olympus, Japan). The results were shown in FIG. 2. As can be seen from FIG. 2, 50 μM to 400 μM TMP all effectively reduced $Ca^{2+}$ concentration within glioma cells resulting from the treatment with glutamate ($p<0.05$, *=significant difference from the control group).

1-5 Determination of Cell Cycle

The TMP-treated glioma cells were treated with trypsin/EDTA (Biochrom AG, L-2153), shaken off, collected in a 15 ml centrifugation tube, and centrifuged at 900 rpm for 3 minutes. The resulting supernatant was removed and 1 ml PI solution (50 μg/ml PI, 0.1% sodium citrate, and 0.1% Triton X-100) was added. After one hour of dark incubation at room temperature, the intensity of PI fluorescence was read by flow cytometry (FACSort). In the G2/M phase, DNA has been replicated, and thus the intensity of PI fluorescence of cells in the G2/M phase should be two times of that of cells in the G1 phase.

Figure 3:
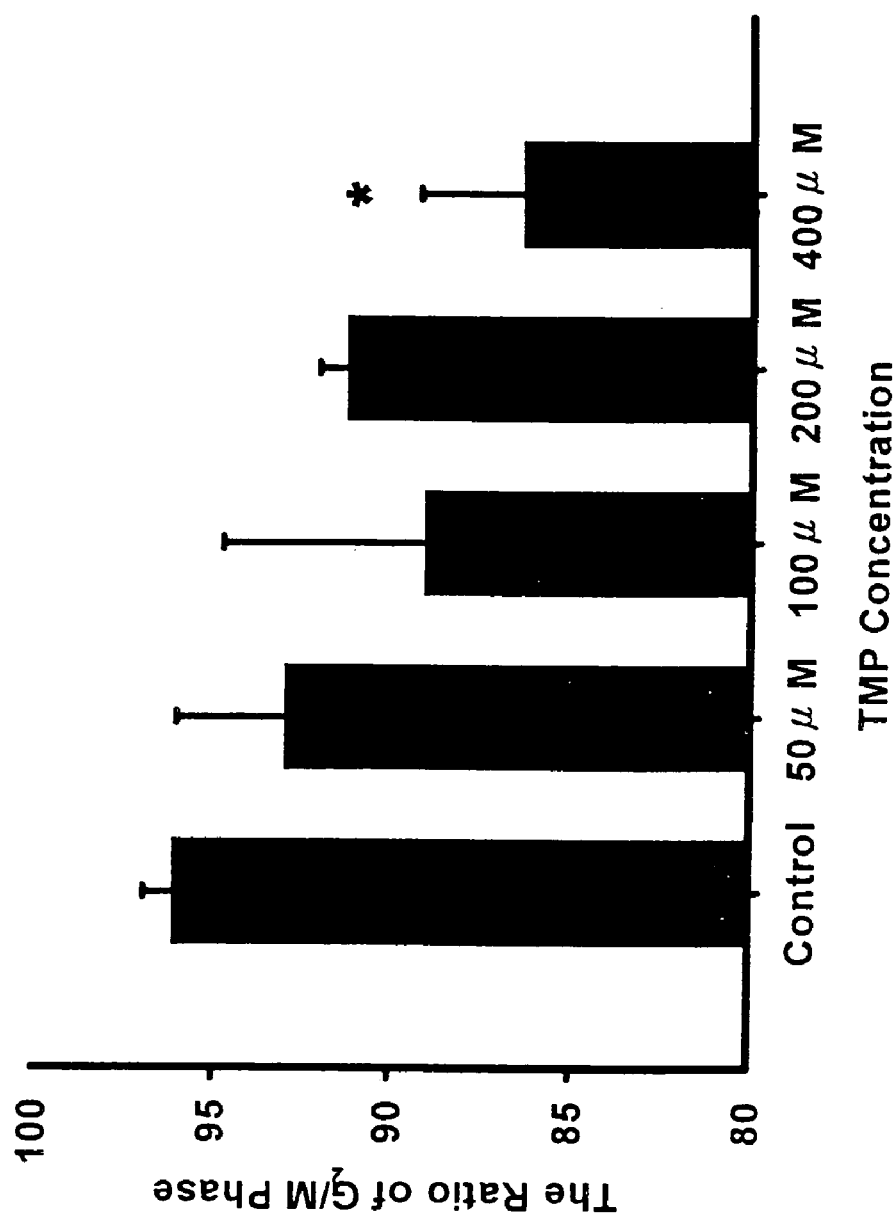
FIG. 3 shows the inhibition of the replication of glioma cells by TMP.

The results are shown in FIG. 3. As can be seen from FIG. 3, 400 μM TMP effectively reduced the ratio of cells in the G2/M phase, implying inhibition of replication of the glioma cells ($p<0.05$, *=significant difference from the control group).

EXAMPLE 2

In Vivo Experiment in Rat 2-1 Animals

Sprague-Dawley (S.D.) rats obtained from the Animal Center of National Yang-Ming University were kept in the following conditions: 12 hours of artificial lightening per day; 22±2° C. air conditioning; sufficient water and food. Eight-week old female rats, weighing 250 to 300 g, were used in the experiments.

2-2 Implantation of Glioma Cells

The rats were anesthetized with chloride hydrate (400 mg/Kg, i.p.) and immobilized on a stereotaxic apparatus (Narishige, Japan). The skin on the head was cut with scissors to expose the skull. Bregma was found as the reference point for the location of microinjection (three-dimensional orientation point: A: 0.7 mm, L; 2.0 mm, H: 2.0 mm). The location was marked with a pen, and the skull at the location was drilled with a drill. Glioma cells ($10^6$ cells) were injected (2 μl/3 mins; total 10 μl) into the frontal cortex of the left brain of the rats with a microinjector.

2-3 Determination of Survival Time

The rats were divided into two groups. The rats of the control group did not receive any treatment following the implantation of glioma cells. The rats of the TMP group received TMP treatment (0.4 mg, subcutaneous injection, twice a day) from the $8^{th}$ day following the implantation. The survival days of rats of the two groups were recorded.

Figure 4:
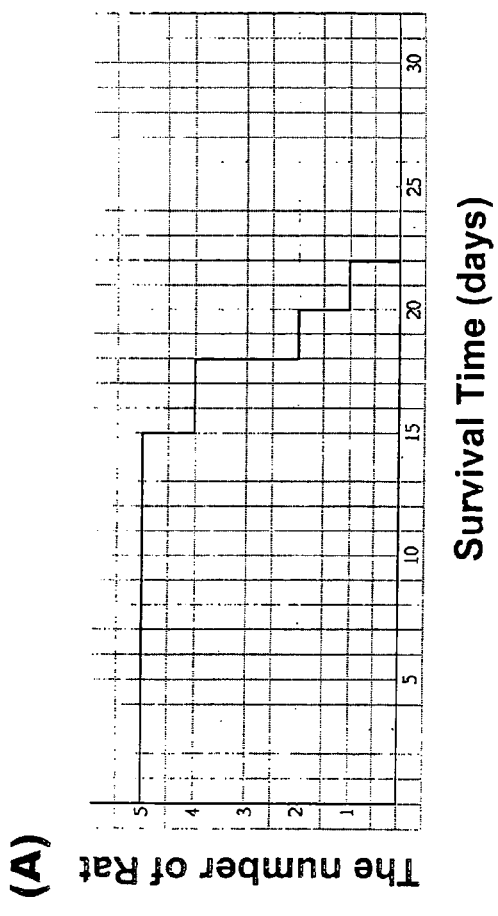
FIG. 4 shows the survival time of rats implanted with glioma cells ((A) the control group; (B) the TMP group.)
Figure 4:
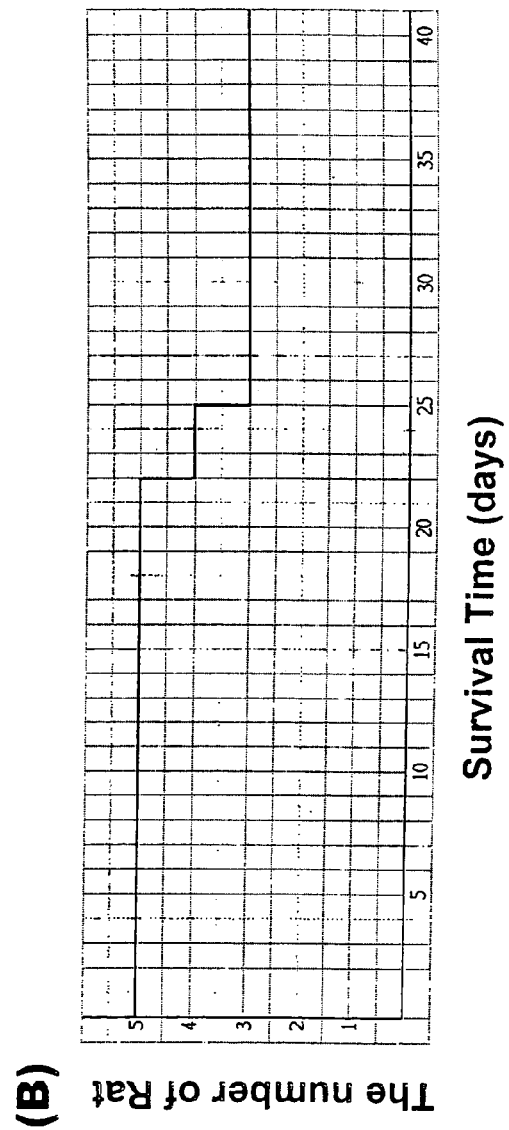

The results are shown in FIG. 4. As can be seen from FIG. 4, rats of the control group died after 15 to 22 days following the implantation (FIG. 4. (A)), while rats of the TMP group survived for at least 22 days following the implantation, half of them even surviving for 40 days (FIG. 4(B)). The results of this experiment showed that TMP could effectively extend the lives of rats suffering from glioma.

2-4 Determination of Activity of Glioma

To determine the activity of glioma cells in the rats, the activity profiles of the tumors were obtained by micro positron emission tomography (micro PET) on the $8^{th}$ and $15^{th}$ day following the implantation of glioma cells. One rat from each of the control and TMP groups was anesthetized with chloride hydrate (400 mg/Kg, i.p.) and injected with $^{18}F$-FDG (800 μCi) in its tail vein. The rats were then put in an incubator for 45 minutes before obtaining the activity profiles of their tumors by micro PET (R4 MicroPET R4, Concorde Microsystem, U.S.A.).

Figure 5:
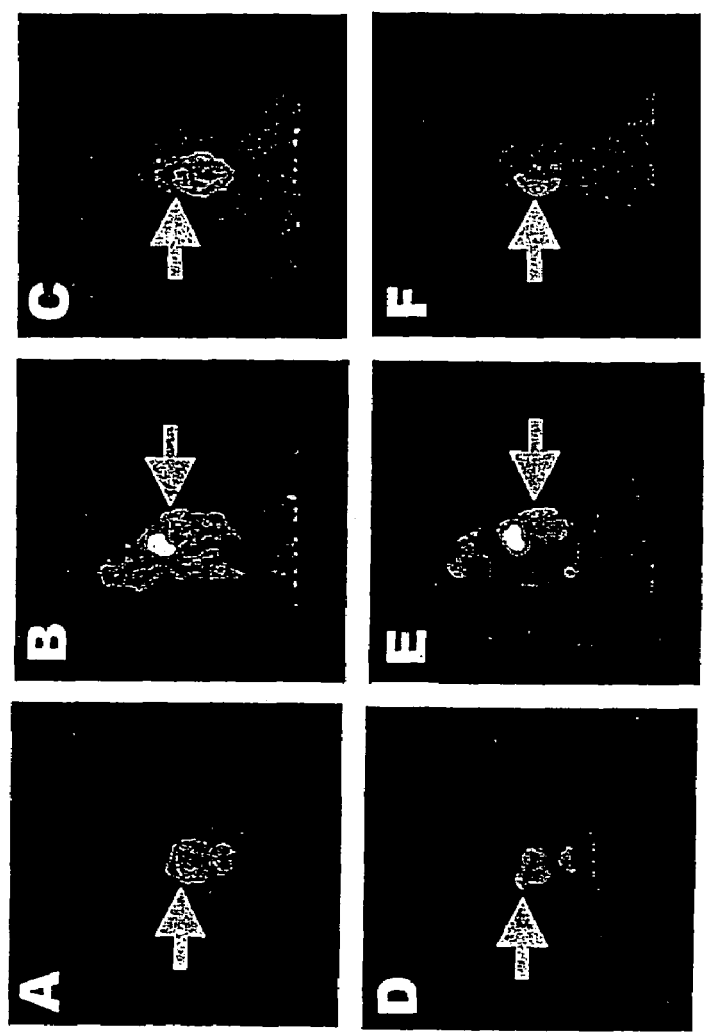
FIG. 5 shows micro positron emission tomography pictures of gliomas in a rat from the control group (pictures A to C: the $8^{th}$ day following implantation; pictures A and D: coronary sectional view; pictures B and E: arrow sectional view; pictures C and F: horizontal sectional view).
Figure 6:
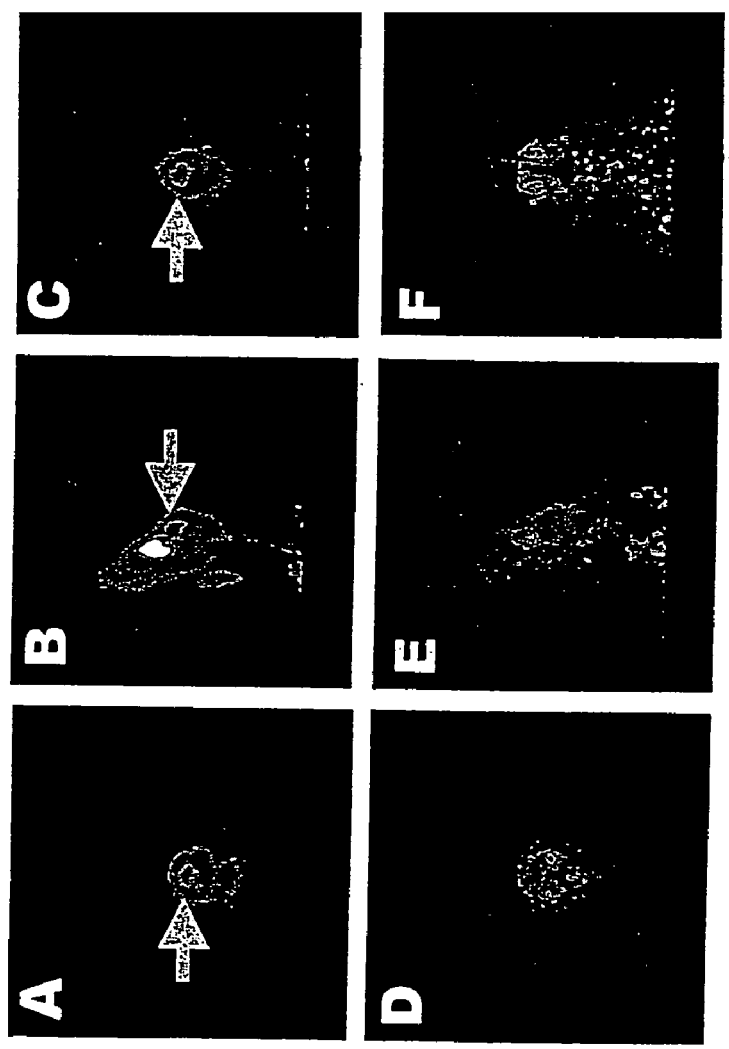
FIG. 6 shows micro positron emission tomography pictures of gliomas in a rat from the TMP group (pictures A to C: the $8^{th}$ day following the implantation of glioma cells; pictures D to F: the $15^{th}$ day following implantation; pictures A and D: coronary sectional view; pictures B and E: arrow sectional view; pictures C and F: horizontal sectional view).

The results are shown in FIGS. 5 and 6. As can be seen from pictures A to C in FIGS. 5 and 6, on the $8^{th}$ day following the implantation of glioma cells, both rats showed an image of a highly activated tumor and inflammation of the surrounding tissue in the implantation area. However, on the 15$^{th}$ day following the implantation, there was no image of a highly activated tumor in the rat from the TMP group (FIG. 6, pictures D to F), while the highly activated tumor in the rat from the control group still exists (FIG. 5, pictures D to F). The results of this experiment showed that TMP could effectively inhibit the activity of glioma in the rats.

We claim:

1. A method for treating brain tumor in a subject in need thereof, comprising administering a therapeutically effective amount of tetramethylpyrazine (TMP) to said subject.

2. The method of claim 1, wherein the brain tumor is a glioma.

3. The method of claim 1, wherein the subject is a mammal.

4. The method of claim 3, wherein the subject is a human.

5. The method of claim 1, wherein the therapeutically effective amount is 5–4000 mg/Kg/day.

6. The method of claim 5, wherein the therapeutically effective amount is 10–1000 mg/Kg/day.

7. The method of claim 6, wherein the therapeutically effective amount is 50–400 mg/Kg/day.

8. The method of claim 1, wherein TMP is administered via injection.

9. The method of claim 2, wherein the subject is mammal.

10. The method of claim 2, wherein the therapeutically effective amount is 5–4000 mg/Kg/day.

11. The method of claim 2, wherein TMP is administered via injection.

* * * * *